US008914127B1

(12) United States Patent
Yan et al.

(10) Patent No.: US 8,914,127 B1
(45) Date of Patent: Dec. 16, 2014

(54) SOUND PROCESSOR APPARATUS WITH SOUND PROCESSING INTEGRATED CIRCUIT THAT INCLUDES AN INTEGRATED POWER SUPPLY MODULE

(71) Applicant: Advanced Bionics AG, Staefa (CH)

(72) Inventors: Jie Yan, Valencia, CA (US); Logan P. Palmer, Santa Monica, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/036,511

(22) Filed: Sep. 25, 2013

(51) Int. Cl.
*A61N 1/00* (2006.01)
*A61B 5/04* (2006.01)
*A61N 1/36* (2006.01)

(52) U.S. Cl.
CPC .................................. *A61N 1/36032* (2013.01)
USPC ................................. 607/57; 607/55; 600/379

(58) Field of Classification Search
USPC ....................................... 607/55, 57; 600/379
See application file for complete search history.

(56) References Cited

U.S. PATENT DOCUMENTS

| | | | |
|---|---|---|---|
| 6,219,580 B1 * | 4/2001 | Faltys et al. ..................... 607/57 |
| 7,085,943 B2 | 8/2006 | Chun et al. | |
| 7,925,906 B2 | 4/2011 | Ranganathan et al. | |
| 2004/0049243 A1 | 3/2004 | Seligman | |

* cited by examiner

*Primary Examiner* — Nicole F Lavert
(74) *Attorney, Agent, or Firm* — ALG Intellectual Property, LLC

(57) ABSTRACT

An exemplary sound processor apparatus included in an auditory prosthesis system includes a linear regulator and a sound processing integrated circuit ("IC"). The linear regulator 1) receives a source voltage signal having a source voltage level and provided by an external power source, 2) drops the source voltage level to an intermediate voltage level, and 3) outputs an intermediate voltage signal having the intermediate voltage level. The sound processing IC 1) performs one or more sound processing operations with respect to an audio signal presented to a patient associated with the auditory prosthesis system, 2) receives the intermediate voltage signal having the intermediate voltage level, 3) converts the intermediate voltage level into one or more supply voltage levels, and 4) outputs one or more supply voltage signals having the one or more supply voltage levels.

20 Claims, 8 Drawing Sheets

SOUND PROCESSOR APPARATUS WITH SOUND PROCESSING INTEGRATED CIRCUIT THAT INCLUDES AN INTEGRATED POWER SUPPLY MODULE

BACKGROUND INFORMATION

Various types of auditory prosthesis systems have been developed to assist patients who have severe (e.g., complete) hearing loss. For example, cochlear implant systems may provide a sense of hearing for sensorineural hearing loss patients by providing electrical stimulation representative of sound directly to stimulation sites within the cochlea. As another example, electro-acoustic stimulation ("EAS") systems may assist patients with some degree of residual hearing in the low frequencies (e.g., below 1000 Hz) by providing acoustic stimulation representative of low frequency audio content and electrical stimulation representative of high frequency content.

Many auditory prosthesis systems include a sound processor apparatus (e.g., a behind-the-ear ("BTE") sound processing unit, a body worn device, etc.) configured to be located external to the patient. The sound processor apparatus may perform a variety of functions, such as processing audio signals presented to the patient, controlling an operation one or more implantable devices (e.g., one or more cochlear implants), and providing power to the one or more implantable devices.

A conventional sound processor apparatus includes a dedicated power supply module that receives a source voltage signal provided by an external power source (e.g., a battery or a power source associated with a programming system) and converts the source voltage signal into regulated voltages used to operate various components of an auditory prosthesis system of which the sound processor apparatus is a part. Unfortunately, the dedicated power supply module occupies a relatively large amount of space within the sound processor apparatus. This may contribute to the sound processor apparatus being undesirably large, bulky, and aesthetically unappealing.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

As will be described in more detail below, an exemplary sound processor apparatus included in an auditory prosthesis system may include a linear regulator and a sound processing integrated circuit ("IC") communicatively coupled one to another. The linear regulator 1) receives a source voltage signal having a source voltage level and provided by an external power source, 2) drops the source voltage level to an intermediate voltage level, and 3) outputs an intermediate voltage signal having the intermediate voltage level. The sound processing IC 1) performs one or more sound processing operations with respect to an audio signal presented to a patient associated with the auditory prosthesis system, 2) receives the intermediate voltage signal having the intermediate voltage level, 3) converts the intermediate voltage level into one or more supply voltage levels, and 4) outputs one or more supply voltage signals having the one or more supply voltage levels. The one or more supply voltage signals may be used to power various other components included in the auditory prosthesis system.

By including power supply components and functionality in the sound processing IC, various benefits may be realized. For example, space occupied by conventional dedicated power supply modules in conventional sound processor apparatuses may be conserved, thereby facilitating a reduction in sound processor apparatus size and/or an increase in sound processor apparatus functionality. Moreover, the systems and methods described herein may optimize power efficiency, minimize power loss, reduce component count, and reduce production cost.

Figure 1:
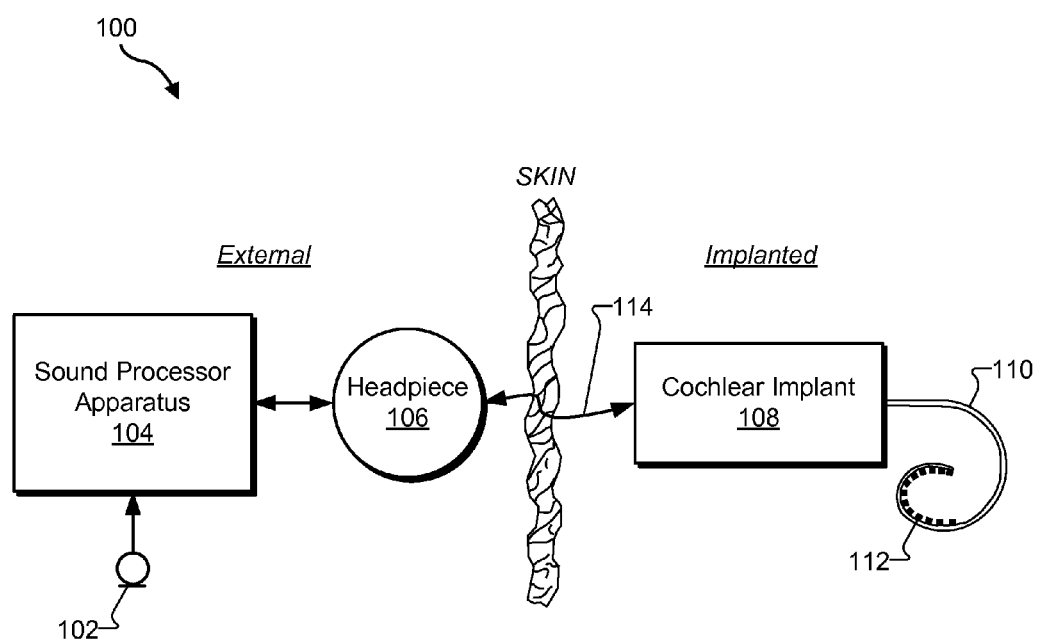
FIG. 1 illustrates an exemplary auditory prosthesis system according to principles described herein.

FIG. 1 illustrates an exemplary auditory prosthesis system 100. As shown, auditory prosthesis system 100 may include various components configured to be located external to a patient including, but not limited to, a microphone 102, a sound processor apparatus 104, and a headpiece 106. Auditory prosthesis system 100 may further include various components configured to be implanted within the patient including, but not limited to, a cochlear implant 108 and a lead 110 with a plurality of electrodes 112 disposed thereon. As will be described in more detail below, additional or alternative components may be included within auditory prosthesis system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor apparatus 104. Additionally or alternatively, microphone 102 may be implemented by one or more microphones disposed within headpiece 106, one or more microphones disposed within sound processor apparatus 104, and/or any other suitable microphone as may serve a particular implementation.

Sound processor apparatus 104 (i.e., one or more components included within sound processor apparatus 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor apparatus 104 may process the one or more audio signals in accordance with a selected sound processing strategy or program to generate appropriate stimulation parameters for controlling cochlear implant 108. Sound processor apparatus 104 may include or be implemented by a behind-the-ear ("BTE") unit, a body worn device, and/or any other sound processing unit as may serve a particular implementation.

In some examples, sound processor apparatus 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor apparatus 104 and may include an external antenna (e.g., a coil and/or one or more wireless communication components) configured to facilitate selective wireless coupling of sound processor apparatus 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor apparatus 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor apparatus 104 (e.g., an audio signal detected by microphone 102) in accordance with one or more stimulation parameters transmitted thereto by sound processor apparatus 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
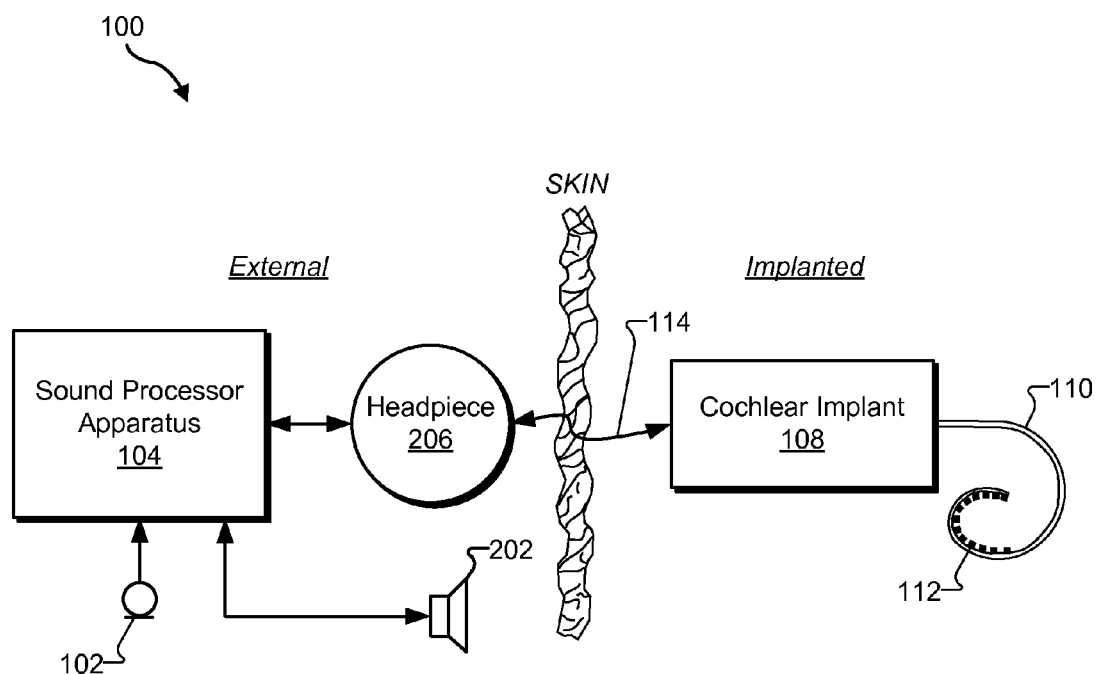
FIG. 2 illustrates an implementation of the auditory prosthesis system of FIG. 1 according to principles described herein.

The auditory prosthesis system 100 illustrated in FIG. 1 may be referred to as a cochlear implant system because sound processor apparatus 104 is configured to direct cochlear implant 108 to generate and apply electrical stimulation representative of audio content (e.g., one or more audio signals) to one or more stimulation sites within the patient by way of one or more of electrodes 112. FIG. 2 illustrates another implementation of auditory prosthesis system 100 in which auditory prosthesis system 100 is further configured to provide acoustic stimulation to the patient. Hence, the implementation shown in FIG. 2 may be referred to as an electro-acoustic stimulation ("EAS") system.

As shown, auditory prosthesis system 100 may further include a receiver 202 (also referred to as a loudspeaker). In this configuration, sound processor apparatus 104 may be configured to direct receiver 202 to apply acoustic stimulation representative of audio content included in a relatively low frequency band (e.g., below 1000 Hz) to the patient and cochlear implant 108 to apply electrical stimulation representative of audio content included in a relatively high frequency band (e.g., above 1000 Hz) to one or more stimulation sites within the patient by way of one or more of electrodes 112.

Figure 3:
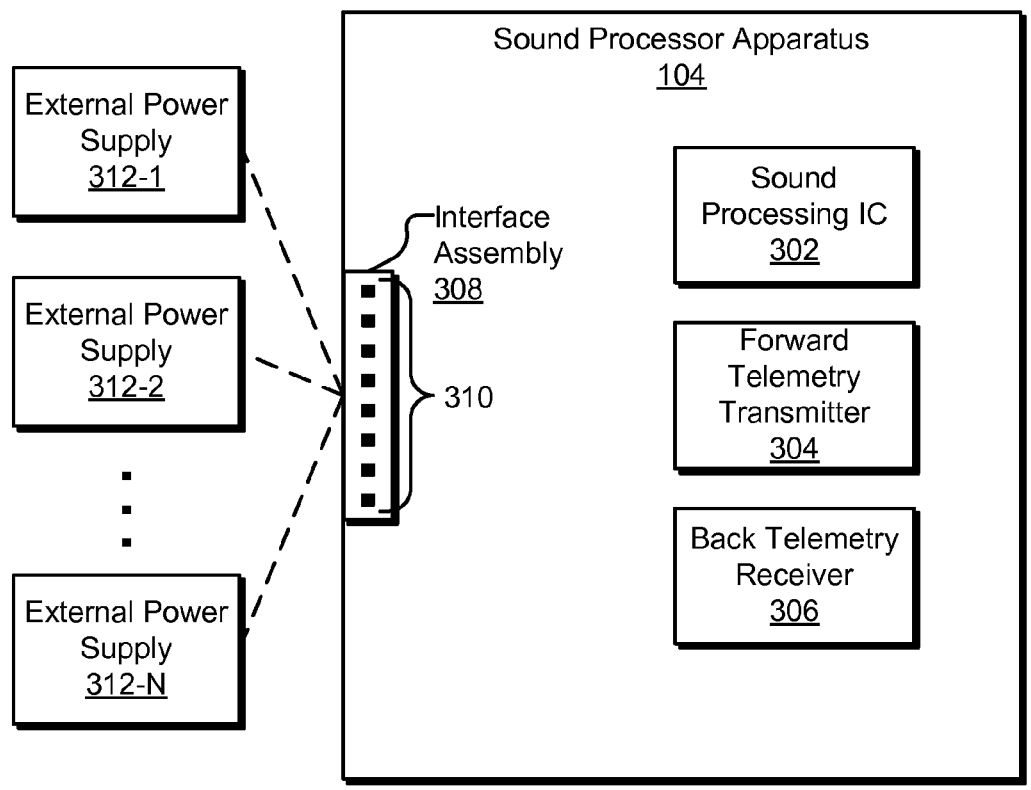
FIG. 3 illustrates exemplary components that may be included within a sound processor apparatus according to principles described herein.

FIG. 3 illustrates exemplary components that may be included within sound processor apparatus 104. As shown, sound processor apparatus 104 may include a sound processing IC 302, a forward telemetry transmitter 304, a back telemetry receiver 306, and an interface assembly 308. Sound processor apparatus 104 may include additional or alternative components as may serve a particular implementation. For example, sound processor apparatus 104 may include one or more additional ICs configured to perform various processing and/or control operations.

Sound processing IC 302 may be implemented by a single chip (e.g., an application-specific IC ("ASIC") (e.g., with a 0.18 um CMOS process) or any other mixed-signal chip containing both digital and analog circuits). In some examples, sound processing IC 302 may perform one or more sound processing operations with respect to an audio signal presented to a patient associated with auditory prosthesis system 100. For example, sound processing IC 302 may perform one or more system control operations associated with auditory prosthesis system 100, one or more signal processing operations, one or more implant diagnostics operations associated with cochlear implant 108, and/or one or more interface operations associated with an external programming system (e.g., a fitting system) for auditory prosthesis system 100, and/or one or more forward telemetry operations. As will be described below, sound processing IC 302 may include an integrated power supply module that generates and provides one or more supply voltage signals used to power various components included within auditory prosthesis system 100.

Forward telemetry transmitter 304 may be implemented by any combination of digital and analog hardware, and may be configured to perform one or more forward telemetry operations. For example, forward telemetry transmitter 304 may transmit control parameters (e.g., stimulation parameters) in the form of one or more radio frequency ("RF") signals to cochlear implant 108 by way of headpiece 206. Such control parameters may direct cochlear implant 108 to generate and apply electrical stimulation and/or perform any other operation.

Back telemetry receiver 306 may be implemented by any combination of digital and analog hardware, and may be configured to perform one or more back telemetry operations.

For example, back telemetry receiver 306 may receive RF signals containing diagnostics data and/or any other data from cochlear implant 108.

Interface assembly 308 may be configured to facilitate interchangeable connectivity of a plurality of external components to sound processor apparatus 104. To this end, interface assembly 308 may include a plurality of contacts 310. The number of contacts 310 may vary as may serve a particular implementation.

In some examples, interface facility 308 may facilitate interchangeable connectivity of a plurality of external power supplies to sound processor apparatus 104. For example, FIG. 3 shows that multiple external power supplies 312 (e.g., external power supplies 312-1 through 312-N) may be interchangeably connected to interface assembly 308 of sound processor apparatus 104 by way of contacts 310. Exemplary external power supplies 312 include, but are not limited to, various types of battery modules (e.g., a rechargeable battery module such as a Li-Ion battery module, a non-rechargeable battery module such as a Zn-Air battery module, etc.), a power supply associated with a programming system (e.g., a fitting device), an off-ear power module, and/or any other type of external power supply as may serve a particular implementation.

Each external power supply may provide a source voltage signal having a unique voltage level. For example, a Li-Ion battery module may provide a source voltage signal having a voltage level in the range of 3.1 volts ("V") to 4.2 V. A Zn-Air battery module may provide a source voltage signal having a voltage level in the range of 2.0 V to 3.0 V. A power source associated with a programming system may provide a source voltage signal having a voltage level of 4.0 V.

However, various components included in auditory prosthesis system 100 may require various different supply voltage levels in order to operate. For example, sound processing IC 302 and other ICs disposed within sound processor apparatus 104 may require a supply voltage level of 1.2 V. Forward telemetry transmitter 304 may require a supply voltage of 1.0-3.0 V. Back telemetry receiver 306 and various auxiliary microphones associated with auditory prosthesis system 100 (e.g., microphone 102) may require a supply voltage level of 2.7 V. The systems and methods described herein may be configured to generate each of these supply voltage levels regardless of the particular external power supply connected to sound processor apparatus 104 at any given time.

Figure 4:
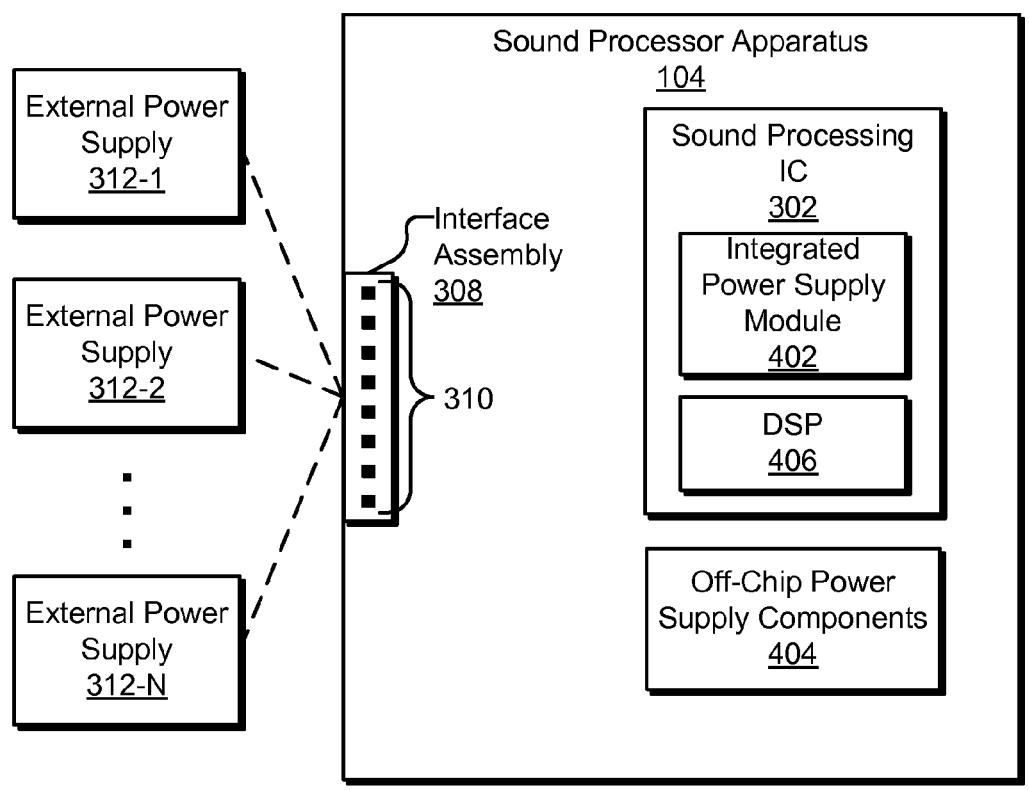
FIG. 4 illustrates exemplary power supply components that may be included within a sound processor apparatus according to principles described herein.

FIG. 4 illustrates exemplary power supply components that may be included within sound processor apparatus 104. As shown, an integrated power supply module 402 may be included within sound processing IC 302. Various other off-chip power supply components 404 (i.e., power supply components that reside outside sound processing IC 302) may also be included within sound processor apparatus 104. An exemplary integrated power supply module 402 and exemplary off-chip power supply components 404 will be described below.

FIG. 4 also shows that sound processing IC 302 may include a digital sound processor ("DSP") 406. DSP 406 may be configured to perform one or more of the sound processing operations described herein. It will be recognized that sound processing IC 302 may additionally or alternatively include any other digital and/or analog components configured to perform the sound processing operations described herein.

As described above, by including integrated power supply module 402 within sound processing IC 302, space occupied by a conventional dedicated power supply module (i.e., a power supply module located entirely off-chip) may be conserved, thereby minimizing a physical size of sound processor apparatus 104 and/or allowing additional functionality (i.e., components) to be added to sound processor apparatus 104.

Figure 5:
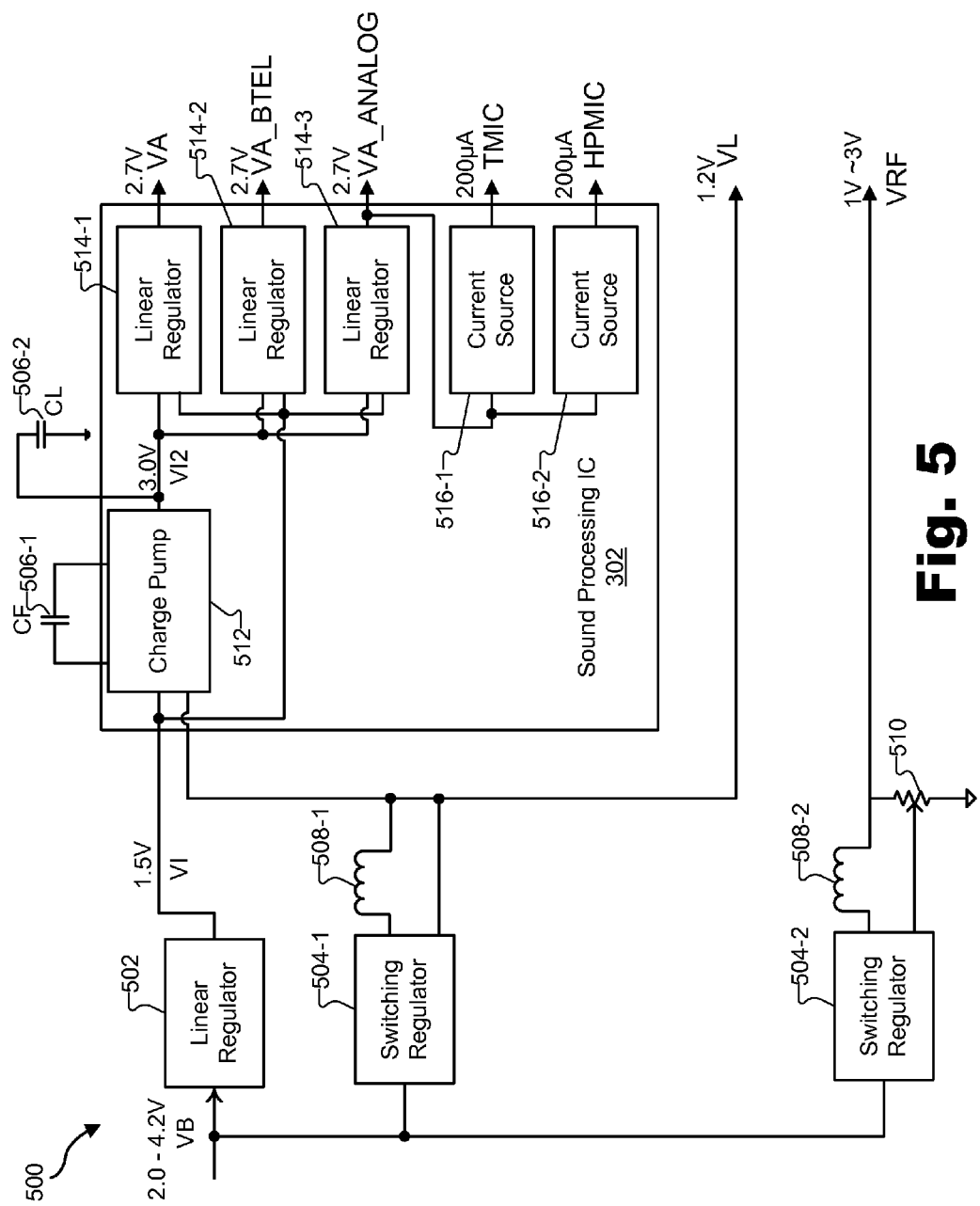
FIG. 5 shows an exemplary implementation of an integrated power supply module and various off-chip power supply components according to principles described herein.

FIG. 5 shows an exemplary implementation 500 of integrated power supply module 402 and off-chip power supply components 404. As shown, implementation 500 may include various components residing outside of sound processing IC 302—a linear regulator 502, switching regulators 504-1 and 504-2 (collectively "switching regulators 504"), capacitors 506-1 and 506-2 (collectively "capacitors 506" and labeled "CF" and "CL"), inductors 508-1 and 508-2 (collectively "inductors 508"), and resistor 510. Each of these components may implement off-chip power supply components 404.

As shown, implementation 500 may also include various components residing within sound processing IC 302—a charge pump 512, a plurality of linear regulators 514 (e.g., linear regulators 514-1 through 514-3), and a plurality of current sources 516 (e.g., current sources 516-1 and 516-2). Each of these components may implement integrated power supply module 402.

The various components shown in FIG. 5 are merely illustrative of the many different on-chip and off-chip power supply components that may be included in sound processor apparatus 104. Each will now be briefly described.

As shown, linear regulator 502 (also referred to as a low drop-out regulator or "LDO") may receive a source voltage signal VB provided by an external power source (e.g., one of the external power sources 312 shown in FIG. 4). The source voltage signal may have any suitable source voltage level. In this particular example, the source voltage signal may have a source voltage level in the range of 2.0 to 4.2 V.

Linear regulator 502 may drop the source voltage level to an intermediate voltage level and output an intermediate voltage signal VI having the intermediate voltage level. In the particular example of FIG. 5, linear regulator 502 drops the source voltage level to 1.5 V. Linear regulator 502 may drop the source voltage level in any suitable manner.

Charge pump 512 may receive the intermediate voltage signal VI having the intermediate voltage level, double the intermediate voltage level, and output an additional intermediate voltage signal VI2 having the doubled intermediate voltage level. In the particular example of FIG. 5, charge pump 512 doubles the intermediate voltage level to 3.0 V. This may be performed in any suitable manner.

Figure 6:
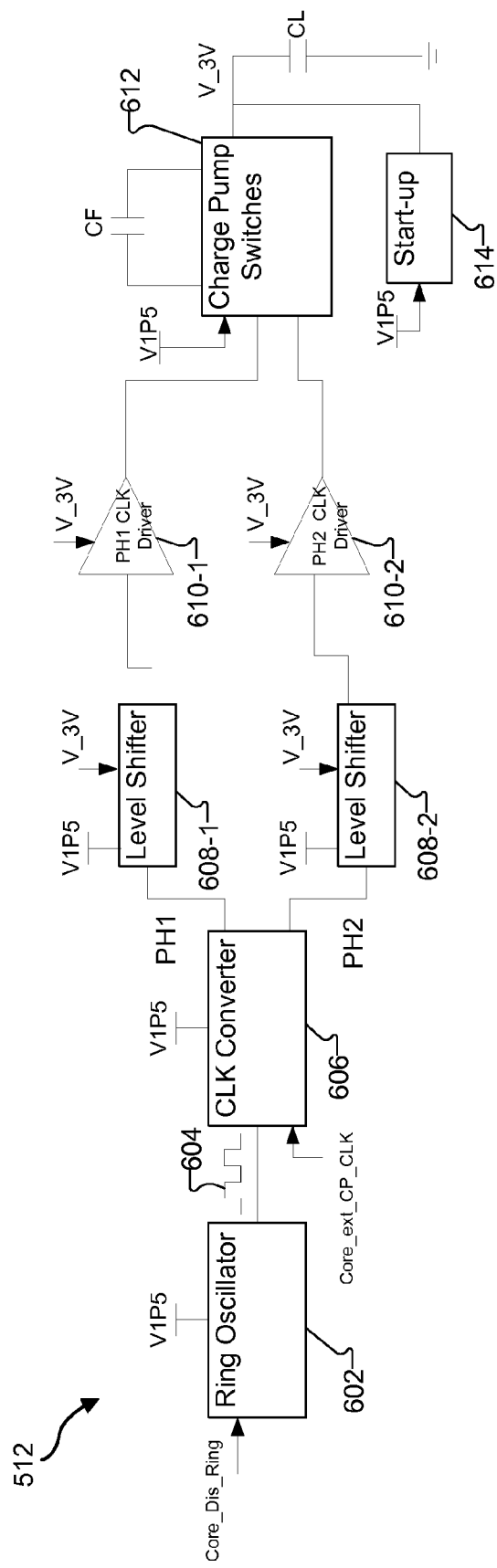
FIG. 6 is an exemplary block diagram of a charge pump according to principles described herein.

FIG. 6 illustrates one way in which charge pump 512 doubles the intermediate voltage level. FIG. 6 is an exemplary block diagram of charge pump 512. As shown, charge pump 512 includes a ring oscillator 602 that generates a clock signal 604 (e.g., a 100 kHz clock signal). A clock converter 606 converts the clock signal 604 to non-overlapping two phase clock signals PH1 and PH2. Two level shifters 608-1 and 608-2 convert clock signals PH1 and PH2 from V1P5 to V_3V voltage level. Clock drivers 610-1 and 610-2 provide switching clock control signals to charge pump switches 612 so the input voltage V1P5 is doubled to V_3V. Start-up circuit 614 pre-charges V_3V node to V1P5 during a start-up period and provides the voltage for the level shifters 608 until V_3V reaches V1P5. When V_3V reaches V1P5 level the start-up circuit 614 is turned off and V_3V node is isolated from V1P5. V_3V node voltage begins to increase above V1P5 toward the target value by the charge pump 512. Control signal Core_Dis_Ring is used to enable/disable the ring oscillator 602. After the charge pump 512 starts up, the ring oscillator 602 can be disabled. Then a clock signal with programmable frequencies from 20 kHz to 120 kHz can be supplied by Core_ext_CP_CLK for charge pump clock. The charge pump 512 may require two low-ESR capacitors CF and CL (i.e., capacitors 506-1 and 506-2 shown in FIG. 5) connected to charge pump 512 and residing outside sound processing IC 302.

Returning to FIG. 5, linear regulators 514 may receive the additional intermediate voltage signal V12, drop the doubled intermediate voltage level to one or more supply voltage levels, and output one or more supply voltage signals having the one or more supply voltage levels. For example, FIG. 5 shows that each linear regulator 514 drops 3.0 V to 2.7 V and outputs a supply voltage signal of 2.7 V. As shown, linear regulator 514-1 outputs a supply voltage signal VA, which may be used to power one or more digital components included in sound processing IC 302. Linear regulator 514-2 outputs a supply voltage signal VA_BTEL, which may be used to power back telemetry receiver 306. Linear regulator 514-3 outputs a supply voltage signal VA_ANALOG, which may be used to power one or more digital components included in sound processing IC 302 and one or more auxiliary microphones (e.g., microphone 102) included in auditory prosthesis system 100.

Figure 7:
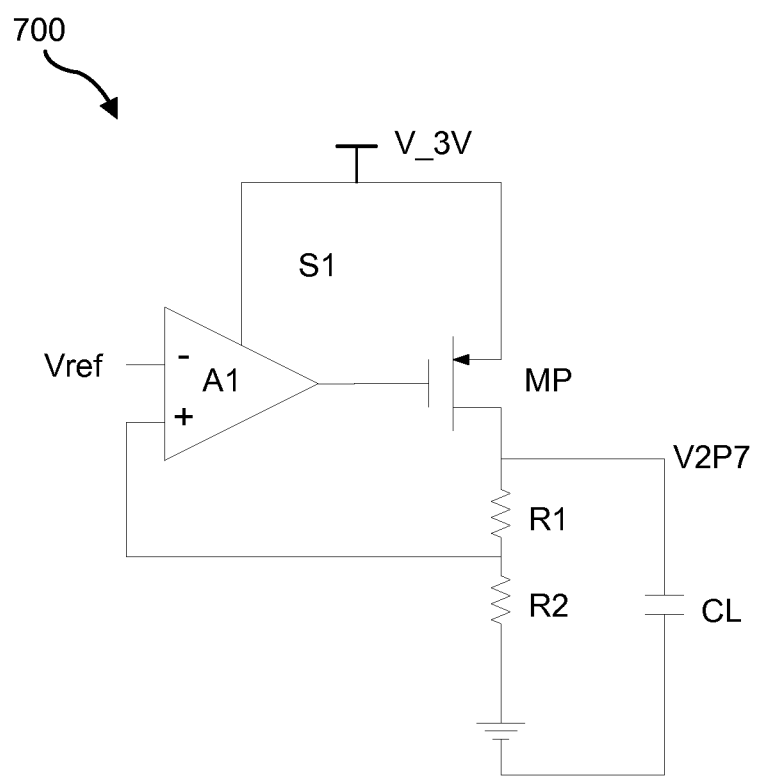
FIG. 7 shows an exemplary topology that may be used for a linear regulator according to principles described herein.

FIG. 7 shows an exemplary LDO topology 700 that may be used for each of linear regulators 514. As shown, topology 700 includes an error amplifier A1, a pass transistor MP, and resistor divider R1 and R2. Error amplifier A1 compares the fraction of the output voltage V2P7 with the reference voltage Vref and adjusts the resistance of pass transistor MP so that the output voltage V2P7 is regulated to 2.7V. In some examples, the intermediate voltage of 1.5 V of intermediate voltage signal VI is used as the reference voltage Vref. This may eliminate the burden to generate an accurate on-chip reference voltage.

Returning to FIG. 5, current sources 516 may provide current for one or more auxiliary microphones (e.g., microphone 102) included in auditory prosthesis system 100. As shown, current sources 516 may generate the current using the supply voltage signal VA_ANALOG.

Switching regulators 504 (also referred to as "buck regulators") may be configured to generate one or more additional supply voltage signals used to power other components within auditory prosthesis system 100. For example, switching regulator 504-1 may receive the source voltage signal VB and use the source voltage signal VB to generate, together with inductor 508-1, a supply voltage signal VL having a supply voltage level of 1.2 V. Supply voltage signal VL may be used to power various components (e.g., various digital components included within sound processing IC 302 and/or one or more other logic components). Likewise, switching regulator 504-2 may receive the source voltage signal VB and use the source voltage signal VB to generate, together with inductor 508-2 and resistor 510, a supply voltage signal VRF having a supply voltage level of 1.0 to 3.0 V. Supply voltage signal VRF may be used to power forward telemetry transmitter 304.

Figure 8:
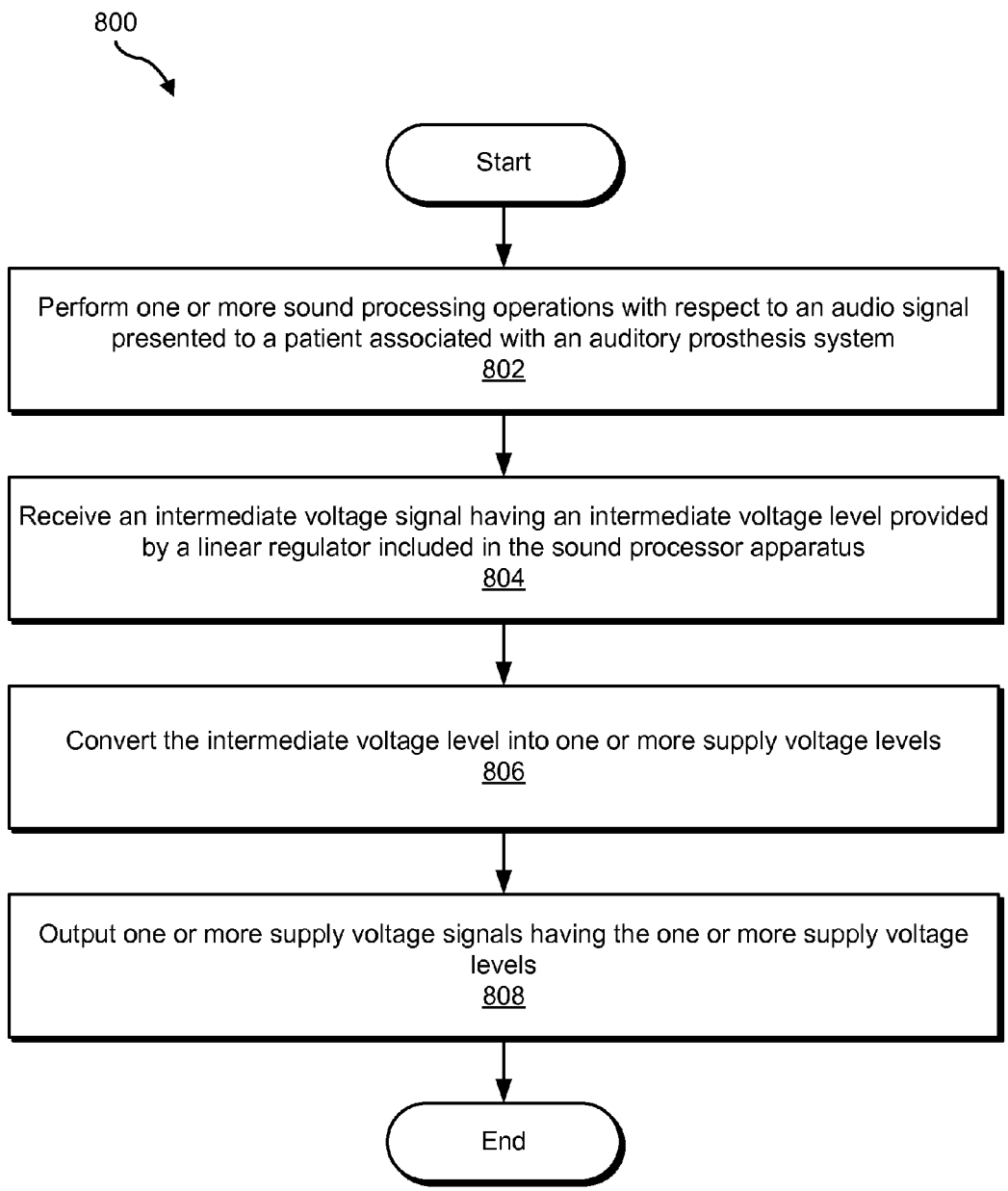
FIG. 8 illustrates an exemplary method according to principles described herein.

FIG. 8 illustrates an exemplary method 800. While FIG. 8 illustrates exemplary steps according to one embodiment, other embodiments may omit, add to, reorder, and/or modify any of the steps shown in FIG. 8. One or more of the steps shown in FIG. 8 may be performed by sound processing IC 302 and/or any implementation thereof.

In step 802, a single integrated circuit included in a sound processor apparatus that is part of an auditory prosthesis system performs one or more sound processing operations with respect to an audio signal presented to a patient associated with an auditory prosthesis system. Step 802 may be performed in any of the ways described herein.

In step 804, the single integrated circuit receives an intermediate voltage signal having an intermediate voltage level provided by a linear regulator included in the sound processor apparatus. Step 804 may be performed in any of the ways described herein.

In step 806, the single integrated circuit converts the intermediate voltage level into one or more supply voltage levels. Step 806 may be performed in any of the ways described herein.

In step 808, the single integrated circuit outputs one or more supply voltage signals having the one or more supply voltage levels. Step 808 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor apparatus external to a patient and included in an auditory prosthesis system associated with the patient, the sound processor comprising:
   a linear regulator that
      receives a source voltage signal having a source voltage level and provided by an external power source,
      drops the source voltage level to an intermediate voltage level, and
      outputs an intermediate voltage signal having the intermediate voltage level;
   a sound processing integrated circuit communicatively coupled to the linear regulator and that
      performs one or more sound processing operations with respect to an audio signal presented to the patient,
      receives the intermediate voltage signal having the intermediate voltage level,
      converts the intermediate voltage level into one or more supply voltage levels, and
      outputs one or more supply voltage signals having the one or more supply voltage levels.

2. The sound processor apparatus of claim 1, wherein the sound processing integrated circuit comprises:
   a charge pump that
      receives the intermediate voltage signal having the intermediate voltage level,
      doubles the intermediate voltage level, and
      outputs an additional intermediate voltage signal having the doubled intermediate voltage level; and
   one or more linear regulators that
      receive the additional intermediate voltage signal,
      drop the doubled intermediate voltage level to the one or more supply voltage levels, and
      output the one or more supply voltage signals having the one or more supply voltage levels.

3. The sound processor apparatus of claim 2, wherein:
   the source voltage level is greater than or equal to 2.0 volts;
   the intermediate voltage level is substantially equal to 1.5 volts;
   the doubled intermediate voltage level is substantially equal to 3.0 volts; and
   the one or more supply voltage levels are substantially equal to 2.7 volts.

4. The sound processor apparatus of claim 2, further comprising a fly capacitor connected to the charge pump and residing outside the sound processing integrated circuit.

5. The sound processor apparatus of claim 2, wherein the one or more linear regulators use the intermediate voltage signal having the intermediate voltage level as a reference voltage signal.

6. The sound processor apparatus of claim 1, further comprising one or more switching regulators residing outside the sound processing integrated circuit and that:
   receive the source voltage signal having the source voltage level;
   generate, based on the source voltage signal, one or more additional supply voltage signals having one or more additional supply voltage levels.

7. The sound processor apparatus of claim 6, wherein the one or more additional supply voltage signals comprises a supply voltage signal used to power the sound processing integrated circuit.

8. The sound processor apparatus of claim 6, wherein the one or more additional supply voltage signals comprises a supply voltage signal used to power a forward telemetry transmitter included the sound processor apparatus.

9. The sound processor apparatus of claim 1, further comprising one or more additional components, wherein the one or more additional components are powered by the one or more supply voltage signals.

10. The sound processor apparatus of claim 1, wherein the sound processing integrated circuit comprises one or more current sources that generate current for one or more microphones included in the auditory prosthesis system.

11. The sound processor apparatus of claim 9, wherein the one or more current sources generate the current using a supply voltage signal included in the one or more supply voltage signals.

12. The sound processor apparatus of claim 1, wherein the external power source is a battery or a power source associated with a programming system communicatively coupled to the sound processor apparatus.

13. The sound processor apparatus of claim 1, wherein:
   the linear regulator
      receives, subsequent to receiving the source voltage signal, an additional source voltage signal having an additional source voltage level and provided by a different external power source,
      drops the additional source voltage level to the intermediate voltage level,
      outputs an additional intermediate voltage signal having the intermediate voltage level;
   the sound processing integrated circuit
      receives the additional intermediate voltage signal having the intermediate voltage level, and
      generates, based on the intermediate voltage signal, one or more additional supply voltage levels having the one or more supply voltage levels.

14. The sound processor apparatus of claim 1, wherein the sound processing integrated circuit performs the one or more sound processing operations by performing at least one of:
   one or more system control operations associated with the auditory prosthesis system;
   one or more implant diagnostics operations associated with a cochlear implant included in the auditory prosthesis system;
   one or more interface operations associated with an external programming system for the auditory prosthesis system; and
   one or more forward telemetry operations.

15. The sound processor apparatus of claim 1, wherein the sound processing integrated circuit is implemented by a single chip.

16. An integrated circuit included in a sound processor apparatus that is external to a patient and a part of an auditory prosthesis system associated with the patient, the integrated circuit comprising:
   a digital signal processor that performs one or more sound processing operations with respect to an audio signal presented to the patient;
   a charge pump that
      receives, from a linear regulator included in the sound processor apparatus, an intermediate voltage signal having an intermediate voltage level,
      doubles the intermediate voltage level, and
      outputs an additional intermediate voltage signal having the doubled intermediate voltage level; and
   one or more linear regulators that
      receive the additional intermediate voltage signal,
      drop the doubled intermediate voltage level to the one or more supply voltage levels, and
      output the one or more supply voltage signals having the one or more supply voltage levels.

17. The integrated circuit of claim 16, wherein the digital signal processor performs the one or more sound processing operations by performing at least one of:
   one or more system control operations associated with the auditory prosthesis system;
   one or more implant diagnostics operations associated with a cochlear implant included in the auditory prosthesis system;
   one or more interface operations associated with an external programming system for the auditory prosthesis system; and
   one or more forward telemetry operations.

18. The integrated circuit of claim 16, wherein:
   the intermediate voltage level is substantially equal to 1.5 volts;
   the doubled intermediate voltage level is substantially equal to 3.0 volts; and
   the one or more supply voltage levels are substantially equal to 2.7 volts.

19. The integrated circuit of claim 16, further comprising one or more current sources that generate current for one or more microphones included in the auditory prosthesis system.

20. A method comprising:
   performing, by a single integrated circuit included in a sound processor apparatus that is external to a patient and part of an auditory prosthesis system associated with the patient, one or more sound processing operations with respect to an audio signal presented to the patient associated with the auditory prosthesis system;
   receiving, by the single integrated circuit, an intermediate voltage signal having an intermediate voltage level provided by a linear regulator included in the sound processor apparatus;
   converting, by the single integrated circuit, the intermediate voltage level into one or more supply voltage levels, and
   outputting, by the single integrated circuit, one or more supply voltage signals having the one or more supply voltage levels.

* * * * *